(12) United States Patent
Faulks et al.

(10) Patent No.: US 7,758,557 B2
(45) Date of Patent: Jul. 20, 2010

(54) REDUCED-NOISE COMPOSITE MATERIALS AND DISPOSABLE PERSONAL CARE DEVICES EMPLOYING SAME

(75) Inventors: Michael J. Faulks, Neenah, WI (US); Jason Wehner, Chicago, IL (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 1218 days.

(21) Appl. No.: 10/719,639

(22) Filed: Nov. 21, 2003

(65) Prior Publication Data

US 2005/0112338 A1 May 26, 2005

(51) Int. Cl.
*A61F 13/15* (2006.01)
*A61F 13/20* (2006.01)
(52) U.S. Cl. .............. 604/385.01; 428/195.1
(58) Field of Classification Search .......... 428/204, 428/156, 160, 195.1; 604/385.23
See application file for complete search history.

(56) References Cited

U.S. PATENT DOCUMENTS

| | | | |
|---|---|---|---|
| 4,376,799 | A | 3/1983 | Tusim |
| 4,433,019 | A | 2/1984 | Chumbley |
| 4,629,643 | A | 12/1986 | Curro et al. |
| 4,663,220 | A | 5/1987 | Wisneski et al. |
| 4,681,793 | A | 7/1987 | Linman et al. |

(Continued)

FOREIGN PATENT DOCUMENTS

CH  683748 A5  5/1994

(Continued)

OTHER PUBLICATIONS

Derwent World Patent Database abstract of KR 2002-013823 A: Description of Cho et al./Khai Club Co. Ltd., "Apparatus for Measuring Friction Sound of Textile Fabric."

*Primary Examiner*—Melanie J Hand
(74) *Attorney, Agent, or Firm*—H. Michael Kubicki

(57) ABSTRACT

A method to reduce the noise produced by movement of a substrate is disclosed. One embodiment of the method includes applying a noise-reducing coating material at an add-on rate of at least about three grams per square meter to a target region of a first surface of a substrate so as to substantially completely coat the target area, wherein the noise-reducing coating material comprises a polymeric material. Also disclosed is a reduced-noise composite material that can be employed in a disposable personal care device. The reduced-noise composite material can include a substrate layer which defines a first surface having a surface area and a target area, and a noise-reducing layer which substantially completely coats the target region. The noise-reducing layer has a basis weight of at least about three grams per square meter. Also disclosed is a reduced-noise disposable personal care device, which may in particular embodiments be a disposable absorbent article. One embodiment of the disposable absorbent article includes a body-side liner and a garment-side outer cover. The outer cover includes a liquid-impermeable substrate layer comprised of a thermoplastic, polymeric material and which defines a first surface having a surface area and a target area. The outer cover further includes a noise-reducing layer which substantially completely coats the target region, and which has a basis weight of at least about three grams per square meter. The disposable absorbent article further includes an absorbent assembly disposed between the body-side liner and the garment-side outer cover.

5 Claims, 9 Drawing Sheets

U.S. PATENT DOCUMENTS

| | | |
|---|---|---|
| 4,704,116 A | 11/1987 | Enloe |
| 4,718,898 A | 1/1988 | Puletti et al. |
| 4,772,444 A | 9/1988 | Curro et al. |
| 4,824,718 A | 4/1989 | Hwang |
| 4,846,821 A | 7/1989 | Lyons et al. |
| 4,902,553 A * | 2/1990 | Hwang et al. ............... 428/156 |
| 4,940,464 A | 7/1990 | Van Gompel et al. |
| 4,942,219 A | 7/1990 | Yatsuka et al. |
| 5,043,205 A | 8/1991 | Perazzo et al. |
| 5,046,272 A | 9/1991 | Vogt et al. |
| 5,104,116 A | 4/1992 | Pohjola |
| 5,224,405 A | 7/1993 | Pohjola |
| 5,226,992 A | 7/1993 | Morman |
| 5,250,343 A | 10/1993 | Stewart |
| 5,254,111 A | 10/1993 | Cancio et al. |
| 5,376,439 A | 12/1994 | Hodgson et al. |
| 5,649,921 A | 7/1997 | Arakawa et al. |
| 5,674,630 A | 10/1997 | Chatterjee |
| 5,753,342 A | 5/1998 | McBride et al. |
| 5,762,643 A | 6/1998 | Ray et al. |
| 5,766,389 A | 6/1998 | Brandon et al. |
| 5,879,341 A | 3/1999 | Odorzynski et al. |
| 5,884,453 A | 3/1999 | Ramsey et al. |
| 5,948,839 A | 9/1999 | Chatterjee |
| 6,096,420 A | 8/2000 | Wilhoit et al. |
| 6,479,154 B1 | 11/2002 | Walton et al. |
| 6,645,190 B1 | 11/2003 | Olson et al. |
| 2003/0120241 A1 | 6/2003 | Sorebo et al. |
| 2004/0075299 A1 * | 4/2004 | Wieber et al. .......... 296/187.02 |

FOREIGN PATENT DOCUMENTS

| | | |
|---|---|---|
| EP | 0 217 032 B1 | 2/1992 |
| EP | 0 661 960 B1 | 8/1997 |
| EP | 661960 B1 * | 8/1997 |
| WO | WO 96/22526 A1 | 7/1996 |
| WO | WO 00/37009 A2 | 6/2000 |

* cited by examiner

REDUCED-NOISE COMPOSITE MATERIALS AND DISPOSABLE PERSONAL CARE DEVICES EMPLOYING SAME

BACKGROUND OF THE INVENTION

The present invention relates to reduced-noise composite materials, to method for making reduced-noise composite materials, and to disposable personal care and health care devices using the aforementioned reduced-noise composite materials. More particularly, the present invention concerns the use of noise-reducing coating materials in disposable personal care devices to reduce the noise caused by movements of the wearer or user.

Many disposable personal care products incorporate thermoplastic, polymeric films to, for instance, provide liquid containment. For example, disposable absorbent articles such as infant diapers, adult incontinence products, disposable training pants, feminine care pads and panties, and the like are intended to collect and completely retain liquid bodily discharges. Other disposable personal care products intended to retain liquid include such devices as, for example, ostomy pouches. Many other devices employ polymeric films as a barrier layer, including, for example, sterile wraps, surgical garb, or other medical products.

Polymeric films are well known in the art as ideal for such applications, because they are easily processable and low enough in cost so as to make the product affordably disposable. Examples of polymeric films suitable for such applications include polyethylene, polypropylene, and the like, and combinations thereof. For example, disposable absorbent articles such as adult incontinence products, infant diapers, and disposable training pants frequently employ a liquid impervious backsheet made of polyethylene, polypropylene, or the like.

However, a major disadvantage of most polymeric films used in disposable personal care devices is that they produce excessive noise under use conditions; that is, "rattling" or "rustling" sounds caused by the wearer's body movements may reveal to others that a disposable personal care article is being worn. Users of certain disposable absorbent articles generally are embarrassed to have to wear such articles. For example, young children several years of age who are not fully toilet trained or who suffer from enuresis (e.g., bedwetting) often must continue to wear diapers, training pants, or disposable underpants. In another example, incontinent adults use disposable absorbent articles designed for adult incontinence. Both groups of users generally are unenthusiastic about advertising the fact that they require the protection of a disposable absorbent article. As a result, the "rattling" or "rustling" sounds associated with disposable absorbent garments employing polymeric backsheets can be greatly embarrassing to the wearer. Such users desire the product to be as discreet as possible.

Various special materials and technologies have been proposed to reduce the level of noise attributable to specific materials. Such special materials and technologies, however, have not been suitable for or compatible with easily processable, low-cost, and mass-produced disposable personal care devices.

Hence, what is lacking and needed in the art is an improved method of reducing the noise produced by substrates employed in disposable personal care devices, reduced-noise composite materials suitable for use in disposable personal care devices, and reduced-noise disposable personal care devices.

BRIEF SUMMARY OF THE INVENTION

In response to the discussed difficulties and problems encountered in the industry, improved reduced-noise composite materials have been invented. The present invention also concerns reduced-noise disposable personal care devices. Furthermore, the present invention concerns methods of making improved reduced-noise composite materials.

As earlier mentioned, many disposable personal care and medical devices employ polymeric substrates which produce noise when subjected to movement by the wearer or user. For discreetness reasons, it is desirable to minimize this noise.

Noise is more easily perceived by the human ear as its level of intensity increases, commonly measured in decibels, which are units for expressing the relative intensity of sound on a common logarithmic scale. Perception of noise is also influenced by the frequencies involved. Generally, the human ear is able to perceive sound having wave frequencies in the range of 16 to 40,000 Hertz (Hz). The human ear has an increased sensitivity to frequencies in the range of 200-5000 Hz, and is particularly sensitive within the range of 2000-4000 Hz, or around the resonant frequency of the auditory canal. Consequently, Applicants have recognized that a reduction in the level of decibels of sound waves having frequencies at or near the range of 2000-4000 Hz produced by the movement of substrates would greatly reduce the ability of the human ear to perceive the noise produced, thus increasing the discreetness of disposable personal care articles employing noise-producing substrates.

One aspect of the present invention concerns a method to reduce noise of a substrate. The method includes applying a noise-reducing coating material at an add-on rate of at least about three grams per square meter to a target region of a first surface of a substrate so as to substantially completely coat the target area, wherein the noise-reducing coating material comprises a polymeric material.

Another aspect of the present invention concerns a reduced-noise composite material, which may in particular embodiments be suitable for use in a disposable personal care device. The reduced-noise composite material include a substrate layer which defines a first surface having a surface area and a target area, and a noise-reducing layer which substantially completely coats the target region. The noise-reducing layer has a basis weight of at least about three grams per square meter.

Yet another aspect of the present invention concerns a reduced-noise disposable personal care device, which may in particular embodiments be a disposable absorbent article. One embodiment of the disposable absorbent article includes a body-side liner and a garment-side outer cover. The outer cover includes a liquid-impermeable substrate layer comprised of a thermoplastic, polymeric material and which defines a first surface having a surface area and a target area. The outer cover further includes a noise-reducing layer which substantially completely coats the target region, and which has a basis weight of at least about three grams per square meter. The disposable absorbent article further includes an absorbent assembly disposed between the body-side liner and the garment-side outer cover.

Another embodiment of the disposable absorbent article to which the present invention relates includes a body-side liner and a garment-side outer cover. The outer cover includes a liquid-impermeable substrate layer constructed of a thermoplastic, polymeric material, and which defines a first surface having a surface area. The disposable absorbent article further includes an absorbent assembly disposed between the body-side liner and the garment-side outer cover. The disposable absorbent article has a Noise Level of less than 30.0 dB at 2 kHz and less than 28.0 dB at 4 kHz.

DETAILED DESCRIPTION OF THE DRAWINGS

The present invention relates, in part, to a method to reduce the noise associated with disposable personal care articles made of substrates that, when subjected to movement by the wearer or user, produce a "rustling" noise. Noise reduction is especially desirable in a disposable personal care articles in which discretion is important to the wearer, such as, for example, a medical device such as an "ostomy" pouch. The present invention is particularly directed to disposable absorbent articles such as disposable baby diapers, disposable training pants, adult incontinence products, feminine care products, disposable swim pants, disposable absorbent underpants, and other, similar articles in which discretion may be a particularly desirable quality.

The method of the present invention involves applying a noise-reducing coating material made of a polymeric material to a noise-producing substrate. The present invention also pertains to reduced-noise composite materials, and yet further pertains to reduced-noise disposable personal care articles employing reduced-noise composite materials. For ease of explanation, the description hereafter will be primarily in terms of reduced-noise composite materials and reduced-noise disposable absorbent articles.

Figure 1:
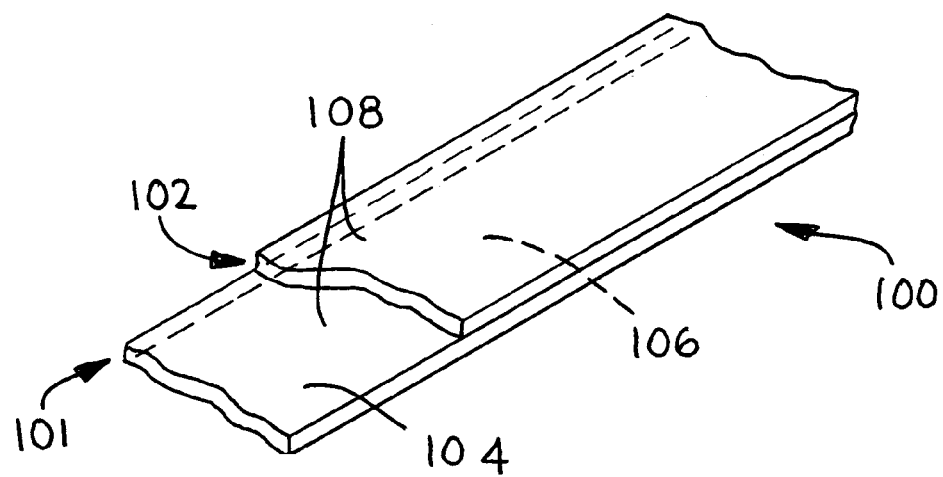
FIG. 1 is a perspective view of an exemplary embodiment of a reduced-noise composite material of the present invention.

As representatively illustrated in FIG. 1, a reduced-noise composite material 100 of the present invention includes a substrate 101 and a noise-reducing coating material 102. The substrate 101, without the aid of a noise-reducing coating material, often produces noise as it moves and buckles. The substrate can be made of any material suitable for use in a disposable personal care device in general and in a disposable absorbent article in particular. The substrate can be made of a non-polymeric substance, such as, for example, paper, tissue, or metal foil, or can be made of a polymeric substance. Polymeric films, such as thermoplastic polymeric films are particularly useful in disposable absorbent articles due to their liquid handling properties, ease of processability, and low cost. For example, various polyolefin-based films are well-known to perform effectively as liquid-impermeable barrier sheets in disposable absorbent articles. "Liquid impermeable," as used herein to describe various substrates, layers, multilayer laminates, and the like, means that a liquid, such as urine, will not pass through the substrate, layer or laminate, under ordinary use conditions, in a direction generally perpendicular to the plane of the substrate, layer or laminate at the point of liquid contact. Polymeric films particularly suitable for use in disposable absorbent articles in conjunction with the present invention include, for example, films comprised of polyethylene, polypropylene, and combinations thereof. Thermoplastic, polymeric films as used in conjunction with the present invention are, in particular embodiments, non-fibrous.

The physical characteristics of the substrate 101 may vary widely depending upon functional, aesthetic, cost, or manufacturing objectives. For example, the substrate can be substantially flat, or can have topographical variations such as projections, ridges, or the like. The substrate can be either apertured or non-apertured depending upon functional or tactile objectives. If the substrate performs a role in the disposable absorbent article requiring liquid impermeability, the substrate is presently preferably non-apertured. For example, if the substrate is a polymeric film acting as a backsheet in a disposable absorbent article such as a disposable training pant, an adult incontinence article, or a feminine care product, substrates presently preferred for such applications include non-apertured, liquid-impermeable, polymeric films. The substrate may be of any thickness suitable to the desired functional, cost, or manufacturing objectives. For example, if the substrate is a polymeric film acting as a backsheet in a disposable absorbent article, its thickness is desirably from about 0.4 mil (0.010 mm) to about 1.5 mils (0.058 mm), more desirably from about 0.5 mils (0.013 mm) to about 1.2 mils (0.030 mm), and still more desirably from about 0.6 mils (0.015 mm) to about 1.0 mils (0.025 mm). The term "mil" as used herein has its customary meaning in the industry, which is a unit of length equal to one thousandth ($10^{-3}$) of an inch (0.0254 mm). Further, the substrate can be impermeable to both liquid and vapor, or can be liquid impervious but vapor pervious. The latter, "breathable" material can be composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn. U.S.A.

The reduced-noise composite material 100 of the present invention also includes at least one noise-reducing coating material 102 made of a polymeric material, attached to the substrate 101. The noise-reducing coating material may be applied at add-on rates that meet the desired noise-reducing objectives. As used herein, the term "add-on rate" refers to the mass of noise-reducing coating material applied per unit of substrate surface area. For example, the noise-reducing coating material can be applied at an add-on rate of about three grams per square meter or greater, and more particularly 3.0 grams per square meter or greater. It is presently believed that add-on rates lower than about three grams per square meter do not deliver sufficient noise reduction benefits, and that add-on rates greater than about fifteen grams per square meter merely create additional cost without providing additional noise reduction benefits. To effectively and efficiently reduce the noise produced by the moving and buckling of a substrate, the add-on rate, in particular embodiments, is about three grams per square meter or greater, more particularly 3.0 grams per square meter or greater, still more particularly about four grams per square meter or greater, yet more particularly 4.0 grams per square meter or greater, still more particularly about five grams per square meter or greater, and yet still more particularly about 5.0 grams per square meter or greater. In particularly desirable embodiments, the add-on rate is less than about fifteen grams per square meter, and more particularly less than about twelve grams per square meter.

Alternatively, the amount of noise-reducing coating material applied may be measured in terms of thickness. For example, the noise-reducing coating material can be at least about 0.1 mil (0.002 mm) thick. It is presently believed that coating amounts lower than about 0.0.1 mil (0.002 mm) thick do not deliver sufficient noise reduction benefits, and that coating amounts greater than about one mil thick merely create additional cost without providing additional noise reduction benefits. To effectively and efficiently reduce the noise produced by the moving and buckling of a substrate, the coating thickness, in particular embodiments, is at least about 0.0.1 mil (0.002 mm), more particularly at least about 0.2 mil (0.005 mm), and still more particularly at least about 0.3 mil (0.008 mm). Additionally, in particular embodiments, the coating thickness is less than about one mil (0.0254 mm), and more particularly less than about 0.8 mils (0.020 mm).

The physical properties of the noise-reducing coating material may vary depending upon functional, cost, or manufacturing objectives. Examples of noise-reducing coating materials suitable for use in the present invention include, but are not limited to, elastomeric materials such as polyisoprene, polybutadiene, polyisobutylene, polyurethanes, silicone rubbers, atactic polypropylene, synthetic block co-polymers such as styrene-butadience-styrene (SBS), styrene-isoprene-styrene (SIS), and styrenethylene-butylene-styrene (SIBS) rubbers, and the like. For example, a suitable noise-reducing coating material is a construction adhesive commercially available from National Starch of Bridgewater, N.J., U.S.A., or a construction adhesive commercially available from Bostik Findley Inc. of Huntingdon Valley, Pa., U.S.A.

The noise-reducing coating material should be applied in such a way that it adequately reduces the noise of the substrate. For example, the coating material can be applied via slot-coat, swirl spray, meltblown spray, or other methods of applying coatings to substrates well known in the art. In particular embodiments, the noise-reducing coating material is applied so as to substantially completely coat a target region 106 of a surface of the substrate to which it is applied (FIG. 1). The phrase "substantially completely coat" as used herein means to create a continuous, complete, unbroken coating subject to occasional uncoated portions as a result of process imperfections as are well known to those skilled in the art. The phrase "target region" as used herein refers to the particular portion of the substrate 101 that is intended to be coated, and can be described in terms of a percentage of a surface area 108 of a first surface 104 of the underlying substrate 101. For example, the noise-reducing coating material could be applied in strips (not pictured) whose cumulative surface area constitutes at least 75% of the surface area 108 of the first surface 104 of the substrate 101. Other alternatives include 100% coverage of the surface area 108, or partial coverage in the form of islands of adhesive. Substantially completely coating the target region of the substrate has been found to be particularly effective at reducing the noise created by the movement of polymer films. Moreover, as the size of the target region increases, the percent surface area of substrate 101 that is coated with the coating material 102 also increases, thus further reducing the substrate's ability to produce noise.

The location and size of the target region may vary depending upon functional, manufacturing, or cost considerations. Desirably, the target region is large in order to reduce the noise produced by the underlying substrate to the greatest extent. For example, if the noise-reducing coating material is used to reduce the noise of a substrate within a disposable absorbent article, the target region in particular embodiments has an area which is at least about 50%, more particularly at least about 75%, still more particularly at least about 85%, and still more particularly at least about 90% of the surface area 108 of the first surface 104 of the underlying substrate 101.

Figure 3:
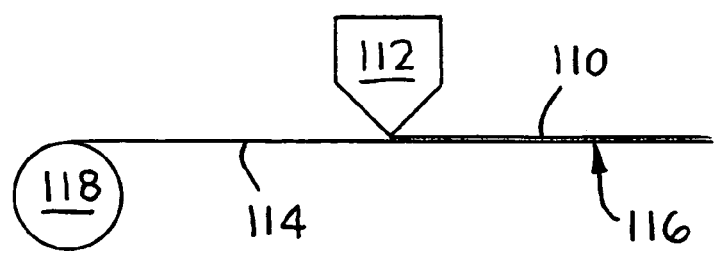
FIG. 3 is a schematic view of an exemplary mode of application of the noise-reducing coating material of the present invention.

One particular method for achieving substantially complete coverage of the target area is via slot-coat application, a method well known to those familiar with the application of adhesive and other coatings to moving substrates. In this method, as representatively illustrated in FIG. 3, a noise-reducing coating material 110 is extruded through a narrow, slit-like nozzle of an extruding device 112 onto a moving web 114 to create the reduced-noise composite material 116. The moving web can be supplied by any variety of supply means 118 well known in the art, such as, for example, a roll unwind. The resulting reduced-noise composite material 116 can subsequently be accumulated for later use by any of several means well known in the art, such as roll-winding, box storage, or the like. Alternatively, the composite material 116 can be routed into a process for the production of a disposable personal care device, such as, for example, a machine designed to produce disposable training pants, disposable diapers, adult incontinence products, feminine care products, or the like. Another way to achieve the desirable substantially complete coverage mentioned above is to supply the noise-reducing coating material as a substantially intact, polymeric web of film which is heated sufficiently to allow it to bond to the substrate, superposing this molten web upon the substrate, and allowing the molten web to cool and solidify upon the substrate (not shown).

The present invention also contemplates the use of the reduced-noise composite material described above in a disposable absorbent article to yield an improved, reduced-noise disposable absorbent article. This reduced-noise disposable absorbent article can take a variety of forms, including, but not limited to, a disposable baby diaper, disposable training pant, adult incontinence product, feminine care product, disposable swim pant, or other, similar articles in which discretion may be a desirable quality. For ease of explanation, the description hereafter will be primarily in terms of a child's disposable training pant. An example of such a training pant is described in U.S. patent application Ser. No. 09/444,083 titled "Absorbent Articles With Refastenable Side Seams" and filed Nov. 22, 1999 by A. L. Fletcher et al., the disclosure of which is incorporated herein by reference to the extent that it is not inconsistent with the present invention.

Figure 4:
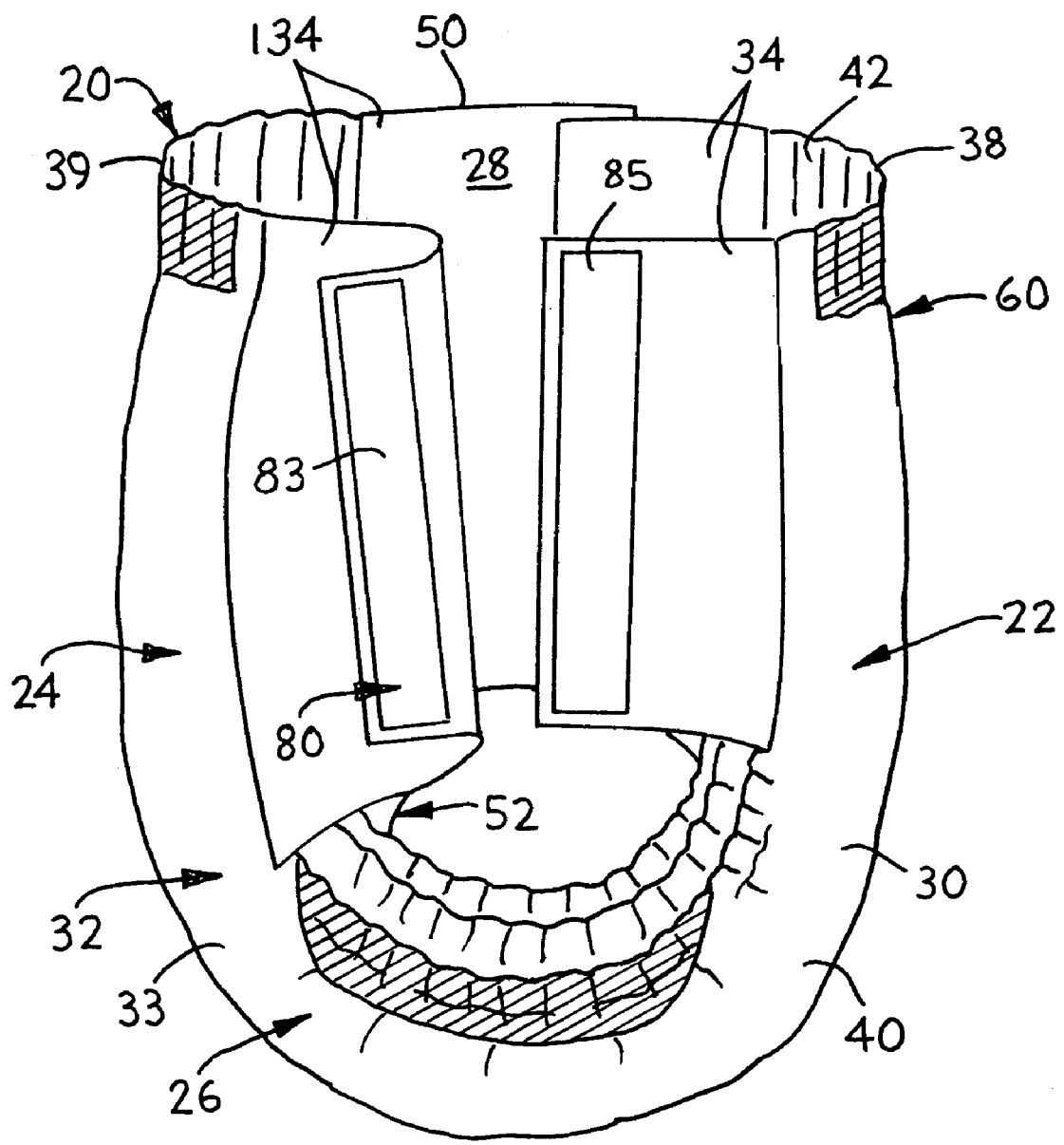
FIG. 4 is a perspective view of an exemplary embodiment of the reduced-noise disposable absorbent article of the present invention.
Figure 5:
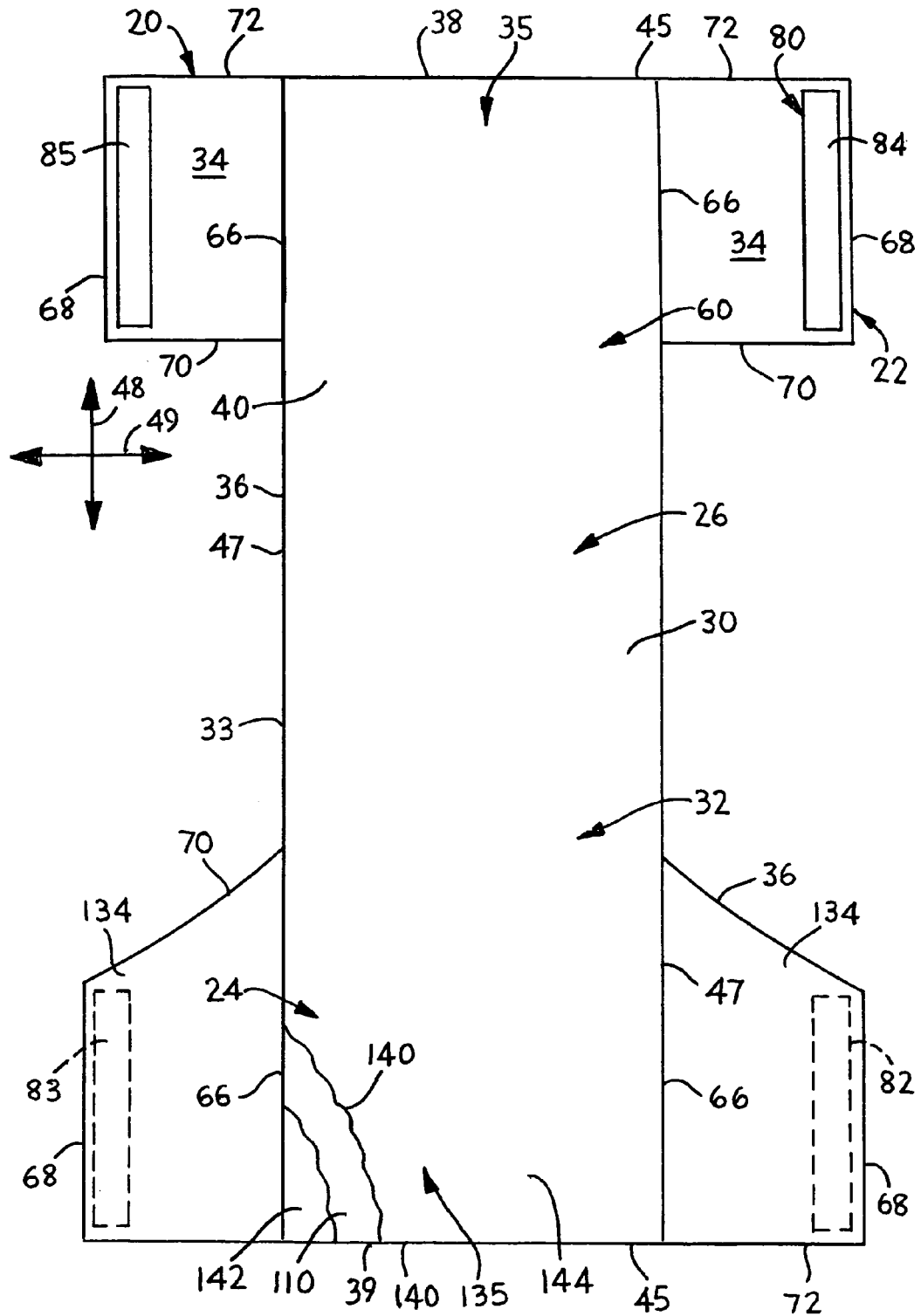
FIG. 5 is a planar view of the garment-facing side of the exemplary embodiment of FIG. 4 in an unfastened condition.
Figure 6:
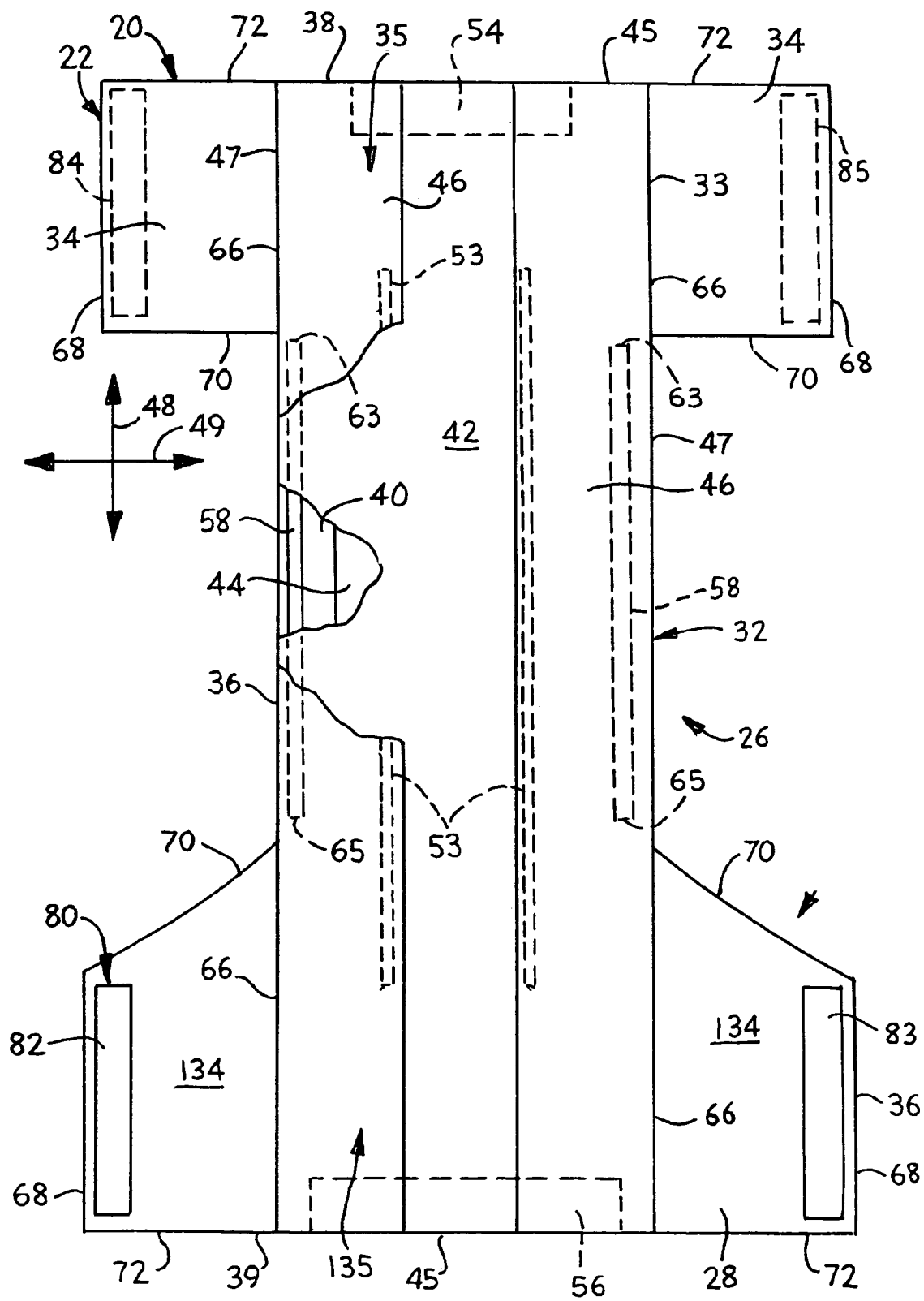
FIG. 6 is a planar view of the body-facing side of the exemplary embodiment of FIG. 4 in an unfastened condition.
Figure 7:
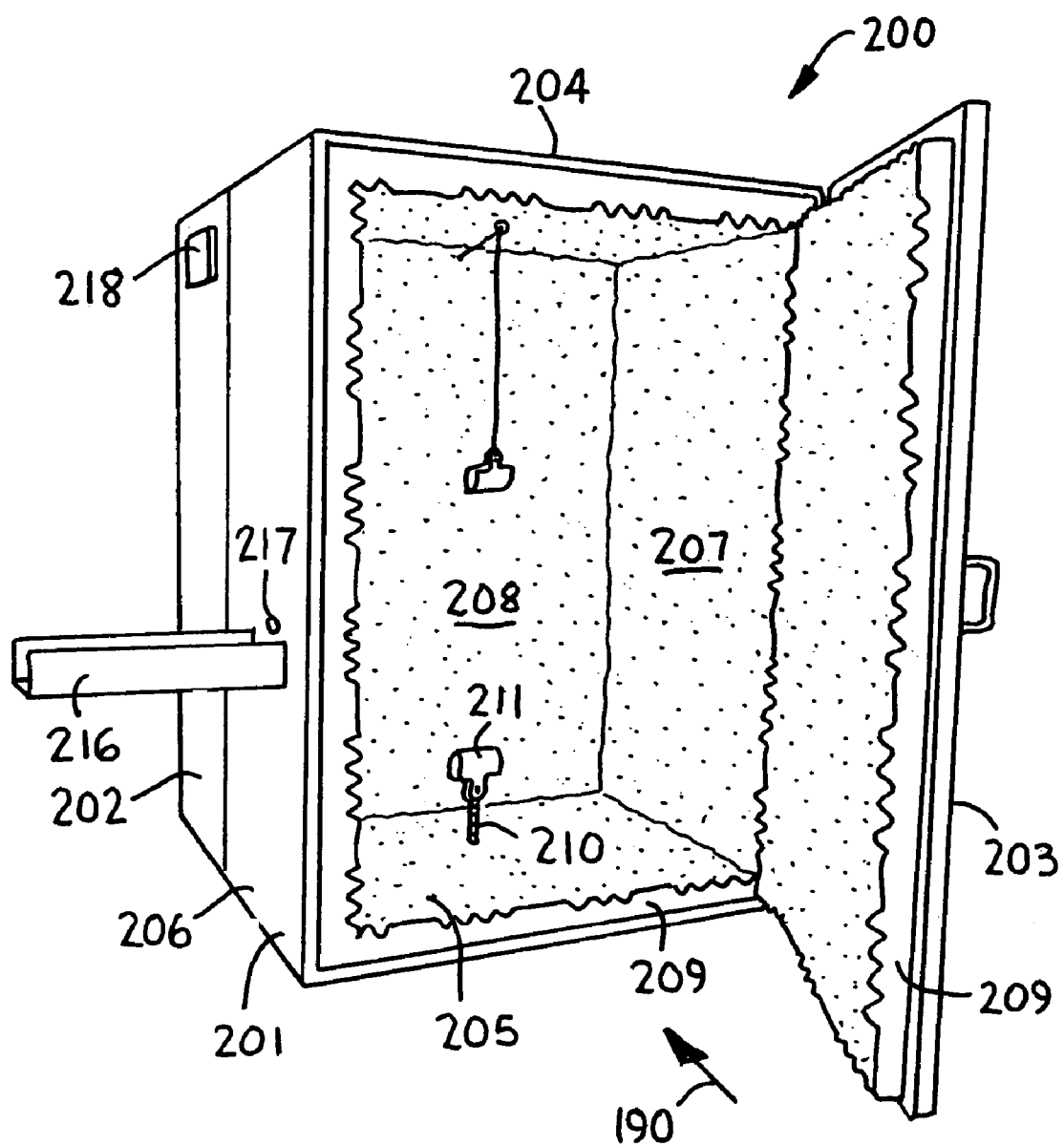
FIG. 7 is a perspective view of the testing apparatus used to evaluate various materials and products, with the apparatus door open.

FIGS. 4-6 representatively illustrate one embodiment of the reduced-noise disposable absorbent article of the present invention in the form of a refastenable, disposable training pant. FIG. 4 shows a perspective side view of the training pant 20 in a partially fastened condition, while FIGS. 5 and 6 show planar views of the garment-facing and body-facing sides, respectively, of the training pant 20 in an unfastened condition. The training pant 20 comprises an absorbent chassis 32 and may include a fastening system 80. The absorbent chassis 32 defines a front waist region 22, a back waist region 24, a crotch region 26 interconnecting the front and back waist regions, an inner surface 28 which is configured to contact the wearer, and an outer surface 30 opposite the inner surface which is configured to contact the wearer's clothing. With additional reference to FIGS. 5 and 6, the absorbent chassis 32 also defines a pair of transversely opposed side edges 36 and a pair of longitudinally opposed waist edges, which are designated front waist edge 38 and back waist edge 39. The front waist region 22 is contiguous with the front waist edge 38, and the back waist region 24 is contiguous with the back waist edge 39.

The illustrated absorbent chassis 32 comprises a rectangular composite structure 33, a pair of transversely opposed front side panels 34, and a pair of transversely opposed back side panels 134. The composite structure 33 and side panels 34 and 134 can be integrally formed or comprise two or more separate elements, as shown in FIG. 4. The illustrated composite structure 33 comprises an outer cover 40, a bodyside liner 42 (FIGS. 4 and 6) which is connected to the outer cover in a superposed relation, an absorbent assembly 44 (FIG. 6) which is located between the outer cover and the bodyside liner, and a pair of containment flaps 46 (FIG. 6). The rectangular composite structure 33 has opposite linear end edges 45 that form portions of the front and back waist edges 38 and 39, and opposite linear side edges 47 that form portions of the side edges 36 of the absorbent chassis 32 (FIGS. 5 and 6). For reference, arrows 48 and 49 depicting the orientation of the longitudinal axis and the transverse axis, respectively, of the training pant 20 are illustrated in FIGS. 5 and 6.

With the training pant 20 in the fastened position as partially illustrated in FIG. 4, the front and back waist regions 22 and 24 are joined together to define a three-dimensional pant configuration having a waist opening 50 and a pair of leg openings 52. The front waist region 22 comprises the portion of the training pant 20 which, when worn, is positioned on the front of the wearer while the back waist region 24 comprises the portion of the training pant which, when worn, is positioned on the back of the wearer. The crotch region 26 of the training pant 20 comprises the portion of the training pant which, when worn, is positioned between the legs of the wearer and covers the lower torso of the wearer. The front and back side panels 34 and 134 comprise the portions of the training pant 20 which, when worn, are positioned on the hips of the wearer.

The front waist region 22 of the absorbent chassis 32 includes the transversely opposed front side panels 34 and a front center panel 35 (FIGS. 5 and 6) positioned between and interconnecting the side panels. The back waist region 24 of the absorbent chassis 32 includes the transversely opposed back side panels 134 and a back center panel 135 (FIGS. 5 and 6) positioned between and interconnecting the side panels. The waist edges 38 and 39 of the absorbent chassis 32 are configured to encircle the waist of the wearer when worn and provide the waist opening 50 which defines a waist perimeter dimension. Portions of the transversely opposed side edges 36 in the crotch region 26 generally define the leg openings 52.

The absorbent chassis 32 is configured to contain and/or absorb any body exudates discharged from the wearer. For example, the absorbent chassis 32 desirably although not necessarily comprises the pair of containment flaps 46 which are configured to provide a barrier to the transverse flow of body exudates. A flap elastic member 53 (FIG. 6) is operatively joined with each containment flap 46 in any suitable manner as is well known in the art. The elasticized containment flaps 46 define an unattached edge which assumes an upright configuration in at least the crotch region 26 of the training pant 20 to form a seal against the wearer's body. The containment flaps 46 can be located along the transversely opposed side edges of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 desirably includes a front waist elastic member 54, a rear waist elastic member 56, and leg elastic members 58, as are known to those skilled in the art (FIG. 6). The waist elastic members 54 and 56 can be operatively joined to the outer cover 40 and/or bodyside liner 42 along the opposite waist edges 38 and 39, and can extend over part or all of the waist edges. The leg elastic members 58 are desirably operatively joined to the outer cover 40 and/or bodyside liner 42 along the opposite side edges 36 and positioned in the crotch region 26 of the training pant 20. The leg elastic members 58 are desirably longitudinally aligned along each side edge 47 of the composite structure 33. Each leg elastic member 58 has a front terminal point 63 and a back terminal point 65, which points represent the longitudinal ends of the elastic gathering caused by the leg elastic members. The front terminal points 63 are desirably located adjacent the longitudinally innermost parts of the front side panels 34, and the back terminal points 65 are desirably located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example, with the application of heat, such that elastic constrictive forces are imparted to the substrate. In one particular embodiment, for example, the leg elastic members 58 comprise a plurality of dry-spun coalesced multifilament spandex elastomeric threads sold under the trade name LYCRA® and available from E. I. Du Pont de Nemours and Company, Wilmington, Del. U.S.A. If, in the construction or application of the containment flaps 46, the waist elastic members 54 and 56, or the leg elastic members 58, a noise-producing substrate, such as, for example, a polymeric film, is used in any fashion, the noise-reducing coating material earlier described can be applied to reduce the noise of the substrate and enhance the discretion of the product consistent with the objectives mentioned earlier.

Figure 2:
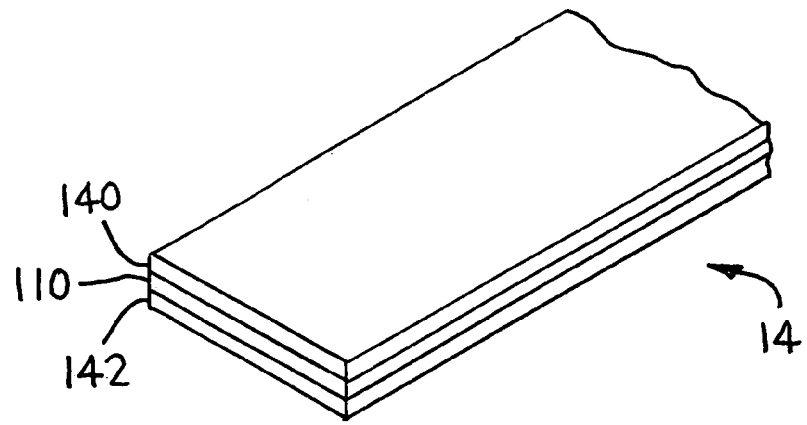
FIG. 2 is a perspective view of an exemplary embodiment of a reduced-noise outer cover of a reduced-noise disposable absorbent article of the present invention.

The outer cover 40 desirably comprises a material that is substantially liquid impermeable, and can be elastic, stretchable or nonstretchable. The outer cover 40 can be a single layer of liquid impermeable material, but desirably comprises a multi-layered laminate structure in which at least one of the layers is liquid impermeable. For instance, as representatively illustrated in FIGS. 2 and 5, the outer cover 40 can include a liquid permeable outer layer 140 and a liquid impermeable inner layer 142 that are suitably joined together by a laminate adhesive, ultrasonic bonds, thermal bonds, or the like. Suitable laminate adhesives, which can be applied continuously or intermittently as beads, a spray, parallel swirls, slot-coat, or the like, can be obtained from Bostik Findley Adhesives, Inc., of Huntingdon Valley, Pa., U.S.A., or from National Starch and Chemical Company, Bridgewater, N.J. U.S.A. The liquid permeable outer layer can be any suitable material and desirably one that provides a generally cloth-like texture. One example of such a material is a 20 gsm (grams per square meter) spunbond polypropylene nonwoven web. The outer layer 140 can also be made of those materials of which the liquid permeable bodyside liner 42 is made. While it is not a necessity for outer layer to be liquid permeable, it is desired that it provides a relatively cloth-like texture to the wearer.

The inner layer 142 of the outer cover 40 can be both liquid and vapor impermeable, or can be liquid impermeable and vapor permeable. The inner layer 142 is desirably manufactured from a thin plastic film, although other flexible liquid impermeable materials can also be used. The inner layer 142, or the liquid impermeable outer cover 40 when a single layer, prevents waste material from wetting articles, such as bedsheets and clothing, as well as the wearer and caregiver. A suitable liquid impermeable film for use as a liquid impermeable inner layer 142, or a single layer liquid impermeable outer cover 40, is a 0.02 mil (0.0005 mm) polyethylene film commercially available from Huntsman Packaging of Newport News, Va. U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn. U.S.A. Any liquid impermeable inner layer 142 or any single layer liquid impermeable outer cover 40 can itself be a reduced-noise composite material as described above. Further, if the outer cover 40 of the disposable absorbent article employs a multilayer design, such as the combination of a liquid permeable outer layer 140 and a liquid impermeable inner layer 142 as just described and representatively illustrated in FIGS. 2 and 5, the multilayer combination can itself be a reduced-noise composite material. For example, in one desirable embodiment, as representatively illustrated in FIG. 5, a noise-reducing coating material 110 may be used in a disposable absorbent article both to reduce the noise of the polymeric, "plastic" inner layer 142 as well as to bond a cloth-like, liquid-permeable outer layer 140 to the inner layer 142, resulting in a reduced-noise composite outer cover 144.

As shown in FIGS. 4 and 5, the training pant 20 and in particular the outer cover 40 desirably comprises one or more appearance-related components such as a registered outer cover graphic 60. The appearance-related components are desirably positioned on the training pant 20 at selected locations, which can be carried out using the methods disclosed in U.S. Pat. No. 5,766,389 issued Jun. 16, 1998 to Brandon et al., which is incorporated herein by reference.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, non-irritating to the child's skin, and can be elastic, stretchable or non-stretchable. Further, the bodyside liner 42 can be less hydrophilic than the absorbent assembly 44, to present a relatively dry surface to the wearer and permit liquid to readily penetrate through its thickness. Alternatively, the bodyside liner 42 can be more hydrophilic or can have essentially the same affinity for moisture as the absorbent assembly 44 to present a relatively wet surface to the wearer to increase the sensation of being wet. This wet sensation can be useful as a training aid. The hydrophilic/hydrophobic properties can be varied across the length, width and depth of the bodyside liner 42 and absorbent assembly 44 to achieve the desired wetness sensation or leakage performance.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. If the bodyside liner employs any noise-producing substrate, such as, for example, a polymeric, plastic film, the noise-reducing coating material earlier described can be applied to reduce the noise of the substrate and enhance the discretion of the product consistent with the objectives mentioned earlier.

Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture comprising Ahcovel N-62 from Hodgson Textile Chemicals of Mount Holly, N.C. U.S.A. and Glucopan 220UP from Henkel Corporation of Ambler, Pa. in an active ratio of 3:1 The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like.

The absorbent assembly 44 (FIG. 6) is positioned between the outer cover 40 and the bodyside liner 42, which components can be joined together by any suitable means such as adhesives, ultrasonic bonds, thermal bonds, or the like. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably comprise a matrix of hydrophilic fibers, such as a web of cellulosic fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich. U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 is generally rectangular in shape, and comprises a blend of wood pulp fluff and superabsorbent material. One preferred type of pulp is identified with the trade designation CR1654, available from U.S. Alliance, Childersburg, Ala. U.S.A., and is a bleached, highly absorbent sulfate wood pulp containing primarily soft wood fibers and about 16 percent hardwood fibers. As a general rule, the superabsorbent material is present in the absorbent assembly 44 in an amount of from about 5 to about 90 weight percent based on total weight of the absorbent assembly. The absorbent assembly 44 suitably has a density within the range of about 0.10 to about 0.50 grams per cubic centimeter. The absorbent assembly 44 may or may not be wrapped or encompassed by a suitable tissue wrap that may help maintain the integrity and/or shape of the absorbent assembly.

The absorbent chassis 32 can also incorporate other materials that are designed primarily to receive, temporarily store, and/or transport liquid along the mutually facing surface with absorbent assembly 44, thereby maximizing the absorbent capacity of the absorbent assembly. One suitable material is referred to as a surge layer (not shown) and comprises a material having a basis weight of about 50 to about 120 grams per square meter, and comprising a through-air-bonded-carded web of a homogenous blend of 60 percent 3 denier type T-256 bicomponent fiber comprising a polyester core/polyethylene sheath and 40 percent 6 denier type T-295 polyester fiber, both commercially available from Kosa Corporation of Salisbury, N.C. U.S.A.

As noted previously, the illustrated training pant 20 has front and back side panels 34 and 134 disposed on each side of the absorbent chassis 32. These transversely opposed front side panels 34 and transversely opposed back side panels 134 can be permanently bonded along attachment lines 66 to the composite structure 33 of the absorbent chassis 32 in the respective front and back waist regions 22 and 24. More particularly, as shown best in FIGS. 5 and 6, the front side panels 34 can be permanently bonded to and extend transversely beyond the linear side edges 47 of the composite structure 33 in the front waist region 22, and the back side panels 134 can be permanently bonded to and extend transversely beyond the linear side edges of the composite structure in the back waist region 24. The side panels 34 and 134 may be attached using attachment means known to those skilled in the art such as adhesive, thermal or ultrasonic bonding. Alternatively, the side panels 34 and 134 can be formed as a portion of a component of the composite structure 33. For example, the side panels can comprise a generally wider portion of the outer cover, the bodyside liner, and/or another component of the absorbent chassis. The front and back side panels 34 and 134 can be permanently bonded together or be releasably attached to one another as illustrated by the fastening system 80.

The illustrated side panels 34 and 134 each define a distal edge 68 that is spaced from the attachment line 66, a leg end edge 70 disposed toward the longitudinal center of the training pant 20, and a waist end edge 72 disposed toward a longitudinal end of the training pant. The leg end edge 70 and waist end edge 72 extend from the side edges 47 of the composite structure 33 to the distal edges 68. The leg end edges 70 of the side panels 34 and 134 form part of the side edges 36 of the absorbent chassis 32. In the back waist region 24, the leg end edges 70 are desirably although not necessarily curved and/or angled relative to the transverse axis 49 to provide greater coverage toward the back of the pant as compared to the front of the pant. The waist end edges 72 are desirably parallel to the transverse axis 49. The waist end edges 72 of the front side panels 34 form part of the front waist edge 38 of the absorbent chassis 32, and the waist end edges 72 of the back side panels 134 form part of the back waist edge 39 of the absorbent chassis.

In particular embodiments for improved fit and appearance, the side panels 34 and 134 desirably have an average length dimension measured parallel to the longitudinal axis 48 that is about 20 percent or greater, and particularly about 25 percent or greater, of the overall length dimension of the absorbent article, also measured parallel to the longitudinal axis 48. For example, in training pants having an overall length dimension of about 54 centimeters, the side panels 34 and 134 desirably have an average length dimension of about 10 centimeters or greater, such as about 15 centimeters. While each of the side panels 34 and 134 extend from the waist opening 50 to one of the leg openings 52, the back side panels 134 are shown as having a continually decreasing length dimension moving from the attachment line 66 to the distal edge 68, as is best shown in FIGS. 5 and 6.

Each of the side panels 34 and 134 can include one or more individual, distinct pieces of material. In particular embodiments, for example, each side panel 34 and 134 can include first and second side panel portions that are joined at a seam, or can include a single piece of material which is folded over upon itself (not shown).

The side panels 34 and 134 desirably although not necessarily comprise an elastic material capable of stretching in a direction generally parallel to the transverse axis 49 of the training pant 20. Suitable elastic materials, as well as one process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material comprises a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Mormon; and European Patent Application No. EP 0 217 032 published on Apr. 8, 1987 in the names of Taylor et al.; all of which are incorporated herein by reference. Alternatively, the side panel material may comprise other woven or nonwoven materials, such as those described above as being suitable for the outer cover 40 or bodyside liner 42, or stretchable but inelastic materials. If the side panels 34 and 134 employ in their construction any material which can produce noise upon being subjected to movement by the wearer, such as, for example, a polymeric, plastic film, the noise-reducing coating material earlier described can be applied to reduce the noise of the substrate and enhance the discretion of the product consistent with the objectives mentioned earlier.

The reduced-noise disposable absorbent article of the present invention may, if in the exemplary form of a disposable training pant as currently being described, be permanently bonded along the side seam and have no fastening system (not shown), or may employ a fastening system 80 as shown in FIGS. 4-6. In one particular embodiment, the illustrated training pant 20 includes a fastening system 80 for refastenably securing the training pant about the waist of the wearer. The illustrated fastening system 80 includes first fastening components 82 and 83 that are adapted to refastenably connect to mating second fastening components 84 and 85. In one embodiment, one surface of each of the first fastening components 82 and 83 comprises a plurality of engaging elements that project from that surface. The engaging elements of the first fastening components 82 and 83 are adapted to repeatedly engage and disengage engaging elements of the second fastening components 84 and 85. The fastening components 82-85 can be adhered to the side panels 34 and 134 by any means known to those skilled in the art such as adhesive bonds, sonic bonds or thermal bonds. In an alternative embodiment, the training pant 20 includes only a single second fastening component disposed in the front waist region 22 for refastenably connecting the first fastening components 82 and 83 (not shown). In a further alternative embodiment, the fastening components can comprise integral portions of the waist regions. For instance, one of the elastomeric front or back side panels can function as second fastening components in that they can comprise a material that is releasably engageable with fastening components disposed in the opposite waist region. Examples of suitable fastening systems are representatively described in U.S. patent application Ser. No. 09/444,083 titled "Absorbent Articles With Refastenable Side Seams" and filed Nov. 22, 1999 by A. L. Fletcher et al., earlier mentioned, and U.S. patent application Ser. No. 09/444,082 titled "Absorbent Article With Non-Irritating Refastenable Seams" and filed Nov. 22, 1999 by L. A. Dimitrijevs et al., the disclosure of which is incorporated herein by reference to the extent not inconsistent with the present invention.

If any part of the fastening system 80, including but not limited to such elements as hook-type fasteners, loop-type fasteners, adhesive fasteners, adhesive-receptive landing zones, and the like, employs in its construction any material which can produce noise upon being subjected to movement by the wearer, such as, for example, a polymeric, plastic film, the noise-reducing coating material earlier described can be applied to reduce the noise of the noise-producing material and enhance the discretion of the product consistent with the objectives mentioned earlier.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

Noise Level Test Procedure

Each of the materials in the examples that follow was tested in a testing apparatus comprised of a test chamber, a control chamber, and a sound level meter. The purpose of the apparatus is to manipulate an article in a controlled noise environment, and to accurately quantify the noise produced by the movement of the article. In general terms, a specimen is secured within the testing chamber, and stretched and relaxed repeatedly. The stretching and relaxing causes the specimen to generate noise which is recorded by the sound level meter.

The testing apparatus used in the examples that follow is illustrated in FIGS. 7-11. The testing apparatus 200 includes a test chamber 201 and a control chamber 202. The test chamber 201 includes a door 203, a top wall 204, a bottom wall 205, two side walls 206 and 207, and a rear wall 208. The door and each wall are constructed of 0.25-inch (0.635 cm) thick 6061 grade anodized aluminum. The door 203 and rear wall 208 are each 36 inches (91.4 cm) in height and 24 inches (61.0 cm) in width. The test chamber side walls 206 and 207 are each 36 inches (91.4 cm) high and 18 inches (45.7 cm) wide. The test chamber top and bottom panels are each 24 inches wide (61.0 cm) and 18 inches (45.7 cm) long. The interior surface of the door 203 and each wall 204-208 has applied thereto two-inch thick polyurethane sound-dampening foam 209, available from Illbruck Inc., a company having offices in Minneapolis, Minn., under the brand name SONEX and stock number SOC-2. As shown, a sound level meter support 216 extends perpendicularly outward from side wall 206 just below a microphone orifice 217. The microphone orifice 217 is positioned 14.5 centimeters above the floor of the bottom wall 205, and is further centered between the door 203 and the rear wall 208. The sound level meter support 216 is constructed of aluminum and is bolted (not shown) to side wall 206.

A lower slide bracket 210, a six-inch (15.24 cm) high Series A1500 Model available from Velmex, Inc., Bloomfield, N.Y., U.S.A., extends from the bottom wall 205 into the test chamber 201, and a lower clamp 211 is affixed to the lower slide bracket 210. An eyelet 212 (FIG. 9) extends from the top wall 204 into the test chamber 201, and a lanyard 213 extends through the eyelet 212. Both the lower bracket 210 and the eyelet 212 are centered both between the side walls 206 and 207 and between the door 203 and the rear wall 208. One end of the lanyard 213 extends into the test chamber 201, and has an upper clamp 214 affixed thereto. The other end of the lanyard 213 extends into the control chamber 202 through a lanyard orifice 215, which is ⅝ inch (16 mm) in diameter. The lanyard used was a premium-braid, 80-lb test Spiderwire®, part number SB80G-300, manufactured by Johnson Worldwide Associates (JWA), Inc., a company having offices in Racine, Wis., U.S.A. Both the lower and upper clamps are two inches wide and were purchased from Tri County Machining, Inc., Appleton, Wis., U.S.A., model 11220.

Figure 8:
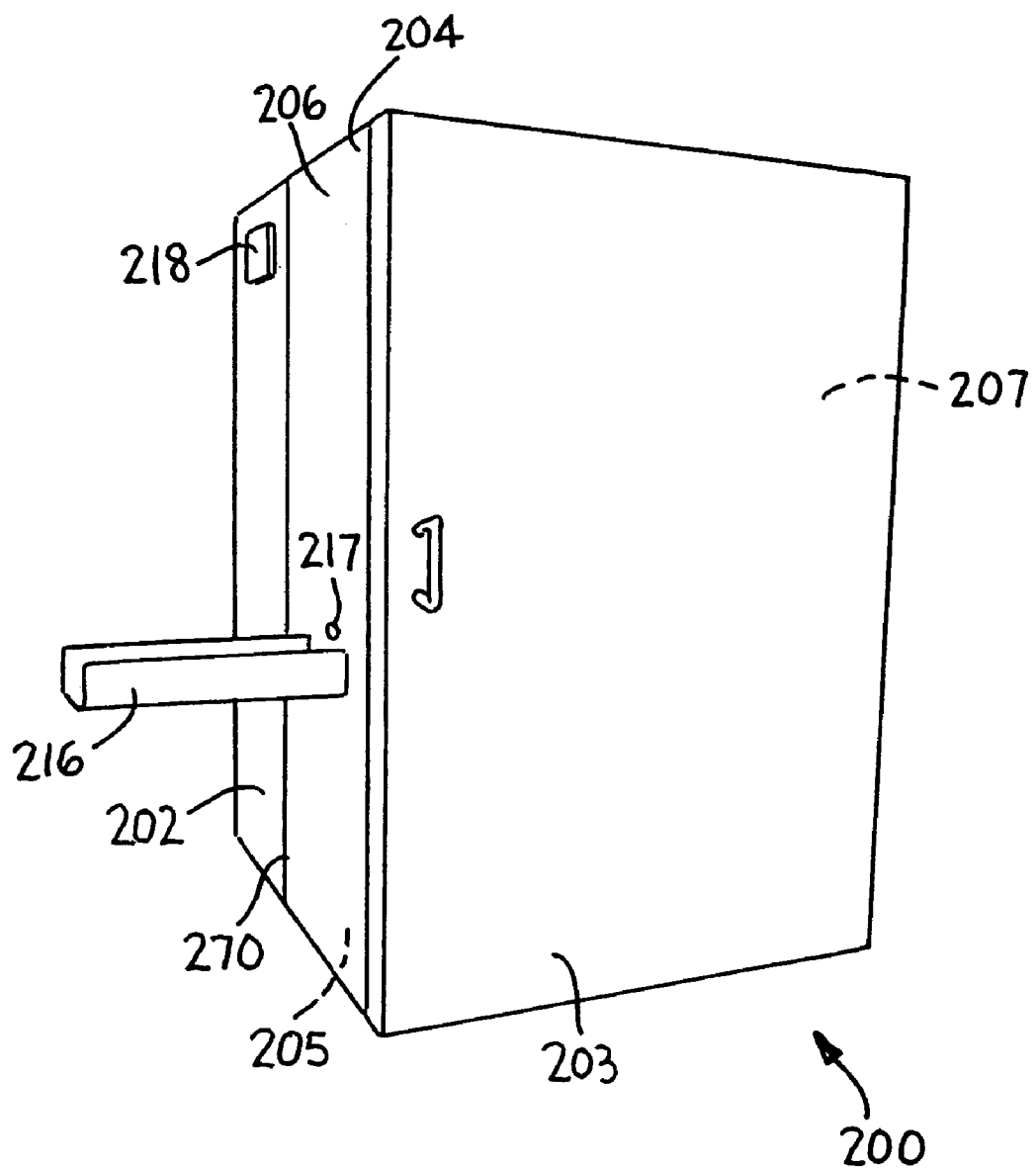
FIG. 8 is a perspective view of the testing apparatus used to evaluate various materials and products, with the apparatus door closed.
Figure 9:
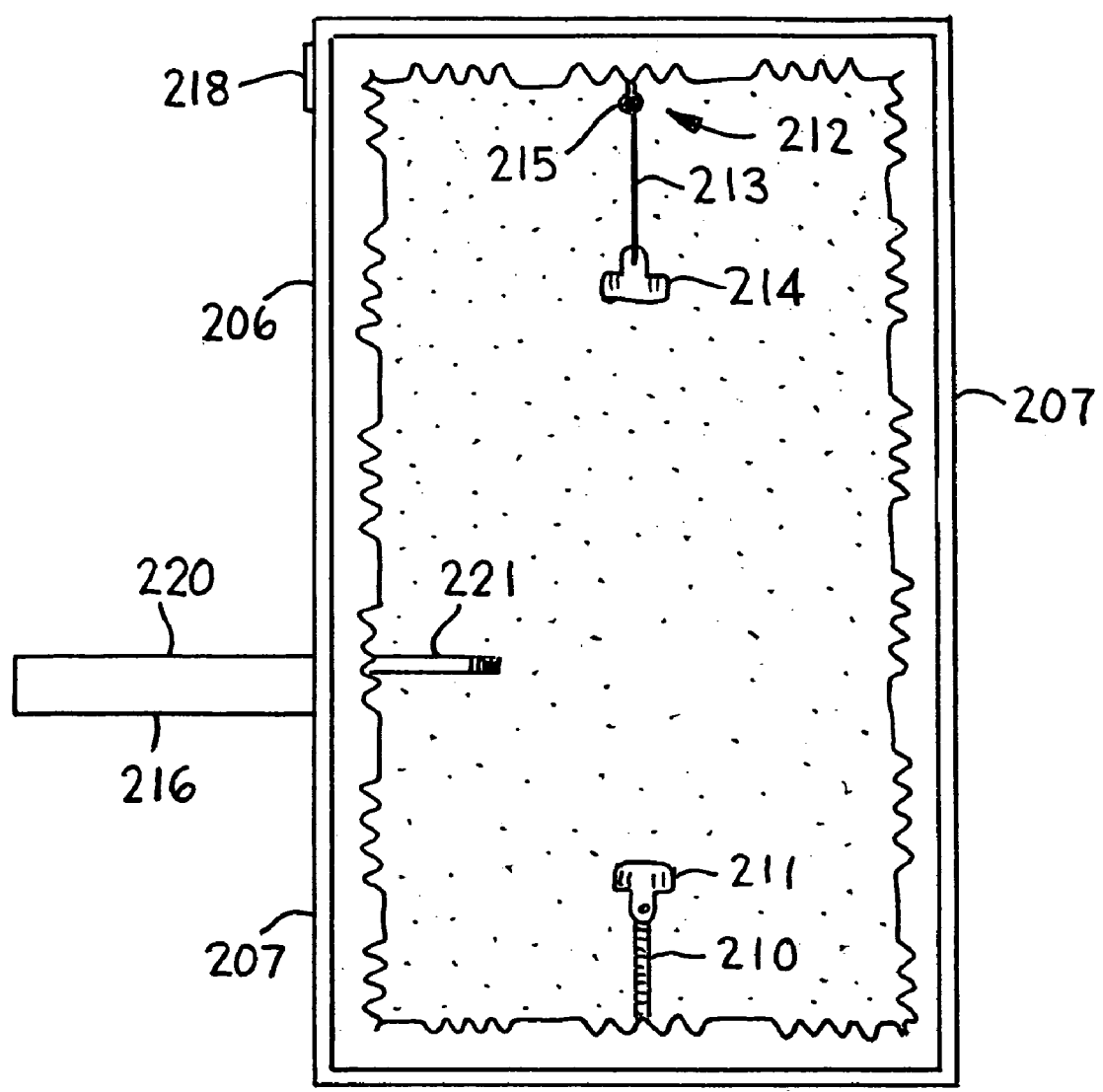
FIG. 9 is a plan view of the apparatus of FIG. 7 taken along arrow 190.
Figure 10:
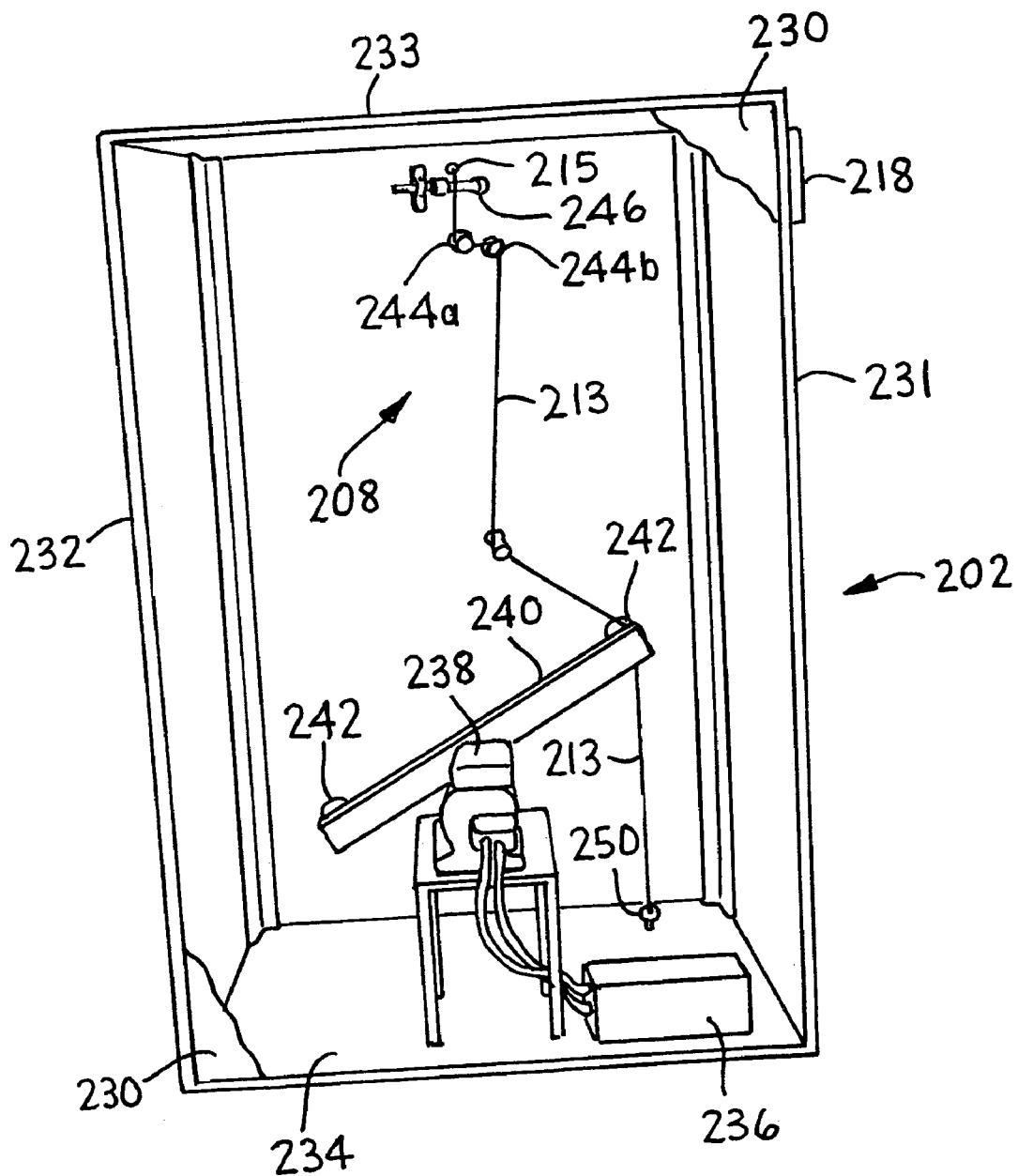
FIG. 10 is an alternative perspective view of the testing apparatus used to evaluate various materials and products, with portions broken away to show underlying features.
Figure 11:
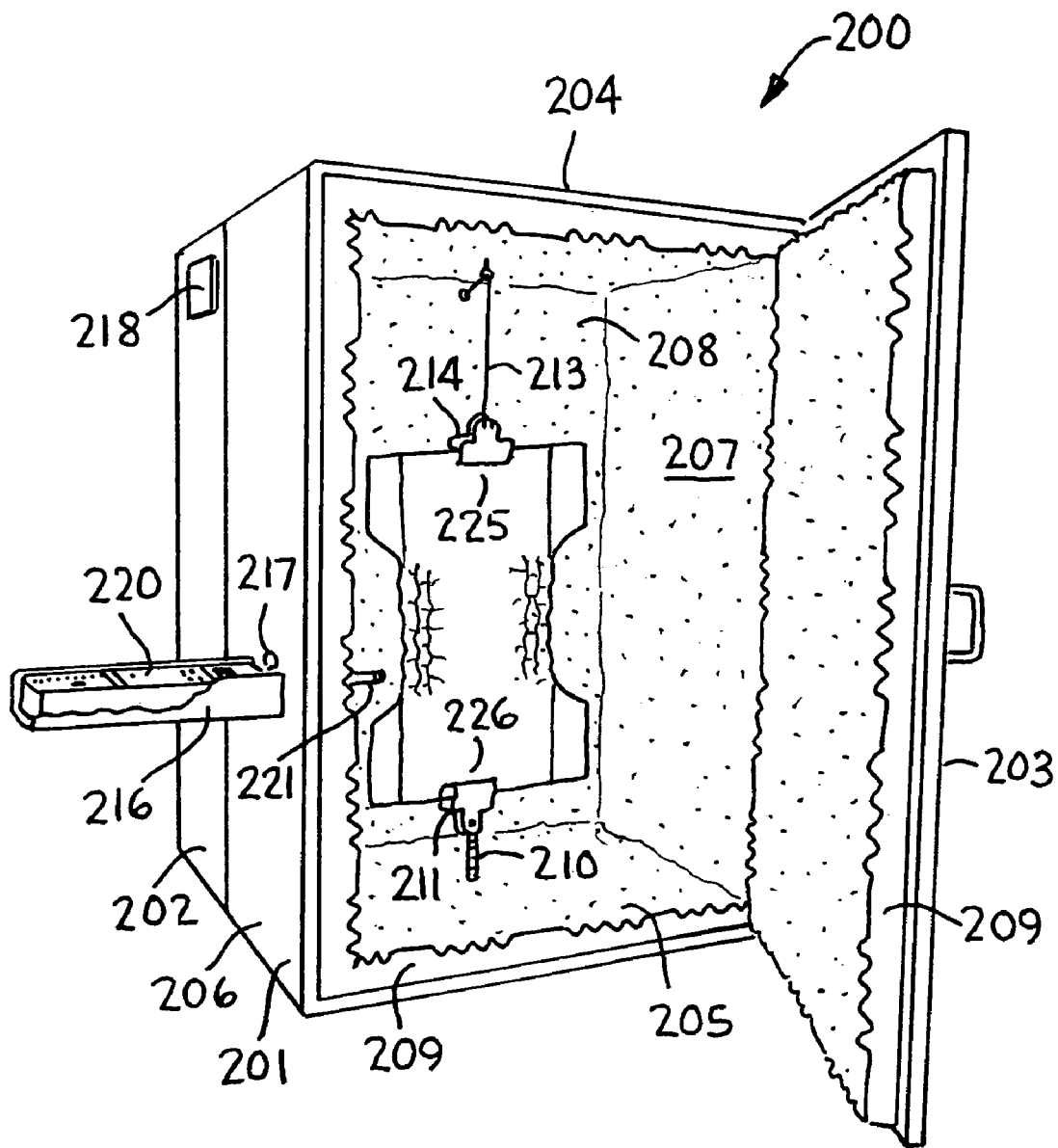
FIG. 11 is a perspective view of the testing apparatus shown in FIG. 7 but with a test specimen secured within the test chamber, and with a sound level meter and microphone.

As shown in FIG. 10, the control chamber 202 includes a front wall 230, two side walls 231 and 232, a top wall 233, and a bottom wall 234. Each wall is constructed of 0.125-inch (0.3175 cm) thick 6061 grade anodized aluminum. The front wall 230 is 36 inches (91.4 cm) high and 24 inches (61.0 cm) wide. The control chamber side walls 231 and 232 are each 36 inches high (91.4 cm) and 12 inches (30.5 cm) wide. The control chamber top and bottom walls 233 and 234 are each 24 inches (61.0 cm) wide and 12 inches (30.5 cm) long. The control chamber 202 is bolted (not shown) to the outer surface of rear wall 208 along seam 270 (FIG. 8). The outer surface of the rear wall 208, and the front wall 230, two side walls 231 and 232, top wall 233, and bottom wall 234 of the control chamber 202 are each coated with 0.600-inch (1.524 cm) thick sound insulating material, part number NYC-600BE, available from Small Parts, Inc., a company having offices in Miami Lake, Fla., U.S.A. The control chamber 202 houses a power supply 236 and a brushless motor 238. The power supply 236 is a 24 volt DC power supply rated for 1.25 amps at 30 watts, model number MSCA-0305, available from Astrodyne Corp., a company having offices in Taunton, Mass., U.S.A. The brushless motor 238 is an AXH series DC brushless gear motor with controller, part number AXH23OKC-50, available from Oriental Motor USA, a company having offices in Chicago, Ill., U.S.A. The motor 238 and motor controller are mounted on an elevated anodized aluminum pad 239. As shown, the motor 238, powered by power supply 236, rotates bar assembly 240 which has a spool bearing 242 at each end. The central axis of the motor spindle is eleven inches (27.9 cm) above the inward surface of the bottom wall 234. The bar assembly 240 is 15 inches (38.1 cm) long, and the spool bearings' axes are spaced 14.5 inches (38.1 cm) apart.

The lanyard 213, which originates in the test chamber 201, enters the control chamber 202 through orifice 215 in the rear wall 208 and passes over a bearing mandrel 246 whose central axis is positioned 3.5 inches (8.89 cm) from the rear wall 208. The lanyard then passes over guide rollers 244a-c, around a spool bearing 242, and is affixed to an eyelet anchor 250. The guide roller 244c is positioned 8.5 inches (21.59 cm) directly above the central axis of the spindle of the motor 238, and the eyelet anchor 250 is positioned 19.5 inches (49.53 cm) from the central axis of the guide roller 244c. When the power supply 236 is activated and the bar assembly 240 rotates, the spool bearings 242 momentarily displace a portion of the lanyard 213 out of the test chamber 201 into the control chamber 202 in a cyclical manner, providing the movement-action required to manipulate the test specimen. During the test procedure, the bar assembly 240 makes a full rotation every four seconds, causing the lanyard 213 and upper clamp 214 to move up and down with the test chamber once-every two seconds, or thirty times per minute. The guide rollers 244a-c, bar assembly 240, spool bearings 242, and eyelet anchor 250 are positioned-such that as the bar assembly 240 rotates, the upper clamp 214 travels a total vertical distance of approximately ten centimeters in each direction. It is contemplated that the positions of the guide rollers 244a-c, bar assembly 240, spool bearings 242, and eyelet anchor 250 could be modified by one of skill in the art, so long as the resulting testing apparatus 200 is configured such that the upper clamp 214 travels a total vertical distance of approximately ten centimeters in each direction during operation of the apparatus 200. The control chamber also includes a start/stop control box 218 secured thereto, which is used to activate and deactivate the power supply 236.

The testing apparatus 200 further includes a sound level meter 220 (FIGS. 9 and 11), such as a model 1900, equipped with a model OB-100 octave filter set, both available from Quest Technologies, a company having offices in Oconomowoc, Wis., U.S.A. The sound level meter is supported by a model QC-20 calibrator and QuestSuite master module software, each also available from Quest Technologies. The software is installed on a personal computer (not shown). During operation of the testing apparatus, the sound level meter 220 rests in the sound level meter support 216. The sound level meter includes a microphone 221 extending 4.75 inches (12 centimeters) therefrom.

Prior to testing a specimen using the testing apparatus 200, the following steps are followed:
1. Calibrate the sound level meter 220 following the instructions in the manufacturer's manual.
2. Insert the full length of the microphone 221 into the testing chamber 201 (it should extend past the wall and sound dampening material approximately 2.5 inches (6.35 cm)), positioned at a 90-degree angle to side wall 206. Allow the sound level meter 220 to rest in the sound level meter support 216.
3. Push the Start button on the control box, without a specimen in the clamps 211/214.
4. Set the octave filter to 2 kHz and take a reading each second for five minutes by activating the sound level meter for five minutes. This allows the amount of noise (at 2 kHz) generated by the testing apparatus alone to be quantified.
5. Repeat step 4 at 4 kHz. This allows the amount of noise (at 4 kHz) generated by the testing apparatus alone to be quantified.

The phrase "at 2 kHz" as used when referring to the amount of noise produced during an experiment and as measured using the testing apparatus 200 means sound waves having frequencies from about 1.414 kHz to about 2.828 kHz. The phrase "at 4 kHz" as used when referring to the amount of noise produced during an experiment and as measured by the testing apparatus 200 means sound waves having frequencies from about 2.828 kHz to about 5.656 kHz.

Having calibrated the testing apparatus 200 and having identified the baseline noise generated thereby, a specimen may be testing in the following manner:
6. Position the upper clamp 214 inside the chamber at its fully retracted (raised) position, by, if necessary, momentarily activating the power supply 236, thereby rotating the bar assembly 240.
7. Position the transverse center portion 225 of one longitudinal end of the test specimen within the upper clamp 214.
8. Raise the lower clamp 211 to its highest position on the lower slide bracket 210. Position the transverse center portion 226 of the other longitudinal end of the test specimen within the lower clamp 211.
9. Lower the lower clamp 211 until the test specimen is taut. "Taut" as used here means that the specimen is elongated to a state such that further elongation would result in permanent deformation to non-elastomeric components of the specimen, such as a non-elastomeric outer cover 40 or body-side liner 42. Close the door 203.
10. Press the Start button to initiate movement of the apparatus and specimen.
11. Set the octave filter to 2 kHz and take a reading each second for one minute by activating the sound level meter for one minute.
12. Set the octave filter to 4 kHz and take a reading each second for one minute by activating the sound level meter for one minute.

13. Repeat Steps 11-12 four more times.
14. Record an average equivalent sound pressure level (LEQ) and a standard deviation thereof at each frequency (for each group of 300 data points).
15. Download the data to a personal computer, such as per the guidelines in the instruction manual accompanying the QuestSuite master module software. Print a copy of the raw data and retain.

EXAMPLES

The noise produced by various prototype and commercially-available products and materials is illustrated in the following examples. The following examples are merely representative and should not be considered as limiting the scope of the invention.

Example 1 demonstrates the sound level within the test chamber with the apparatus turned off and with no test specimen present. Example 2 demonstrates the sound level within the test chamber with the apparatus turned on, but without a test specimen. Examples 3-15 examine the noise produced by a variety of comparative examples in the form of commercial products which employ polymeric backsheet films. Examples 16-19 demonstrate the ability of the noise-reducing coating of the present invention to reduce the noise generated by movement of polymeric films within various prototype articles.

As demonstrated in Example 2, when the testing apparatus is operated without a specimen, average sound levels of about 25.5 dB (std. dev. ~0.16) at 2 kHz and about 21.6 dB (std. dev. ~0.13) at 4 kHz are recorded within the testing chamber due to the operation of the apparatus itself and other ambient noise. When properly constructed, the testing apparatus should produce no more than 26 dB at 2 kHz and 22 dB at 4 kHz when operated without a specimen. When a specimen is tested, the sound level recorded within the chamber is that of the apparatus and the moving specimen combined.

The results of each test are present in the Table below.

Example 1

The door 203 was closed, and steps 11-15 were executed, with the apparatus off at all times and with no specimen in the test chamber. The ambient noise within the sealed chamber was thereby quantified.

Example 2

The door 203 was closed, and steps 10-15 were executed, with no specimen in the test chamber. The noise attributable to the operating apparatus as well as additional ambient noise within the sealed chamber was thereby quantified.

Example 3

In this Example, the noise produced by a LUVS SLEEP-DRYS youth pant (size 65-85 lbs), purchased in 2003 and manufactured by the Proctor and Gamble Company, a corporation having offices in Cincinnati, Ohio, was quantified. This product included a full-length, thermoplastic, polymeric film layer within the outer cover.

Example 4

In this Example, the noise produced by a PULL-UPS GOODNITES youth pant (size 65-85 lbs), obtained in 2002 and manufactured by Kimberly-Clark Corporation, a corporation having offices in Neenah, Wis., was quantified. This product included a full-length, thermoplastic, polymeric film layer within the outer cover, and further included thermoplastic, polymeric film strips within the leakage containment flaps.

Example 5

In this Example, the noise produced by a PULL-UPS GOODNITES youth pant (size 65-85 lbs), obtained in 2003 and manufactured by Kimberly-Clark Corporation, was quantified. This product included a full-length, thermoplastic, polymeric film layer within the outer cover, but, in contrast to Example 4, included no polymeric film within the leakage containment flaps.

Example 6

In this Example, the noise produced by a PAMPERS EASY UPS training pant (size 30-40 lbs), purchased in 2001 and manufactured by the Proctor and Gamble Company, was quantified. This product included a full-length, thermoplastic, polymeric film layer within the outer cover.

Example 7

In this Example, the noise produced by a HUGGIES® PULL-UPS® training pant (size 32-40 lbs) having "Easy Open Sides," obtained in 2002 and manufactured by the Kimberly-Clark Corporation, was quantified. This product included a full-length, thermoplastic, polymeric film layer within the outer cover.

Example 8

In this Example, the noise produced by a TORE PAN MAN training pant (size 9-14 kg), purchased in 2001 in Japan and manufactured by the Unicharm corporation, a corporation having offices in Seattle, Wash., was quantified. This product included a full-length, thermoplastic, polymeric film layer within the outer cover.

Example 9

In this Example, the noise produced by a WALGREENS HIS AND HER training pant (up to 34 lbs size) purchased from WALGREEN'S drugstore, manufactured in 2003 by Associated Hygiene Products, Inc., was quantified. This product included a full-length, thermoplastic, polymeric film layer within the outer cover.

Example 10

In this Example, the noise produced by a CVS SLEEP-PANTS youth pant (size 85-125 lbs) purchased from CVS drugstore, manufactured in 2003 by the Tyco Corp., was quantified. This product included a full-length, thermoplastic, polymeric film layer within the outer cover.

Example 11

In this Example, the noise produced by a WHITE CLOUD training pant (size 38+ lbs), manufactured in 2003 by the Tyco Corp., was quantified. This product included a full-length, thermoplastic, polymeric film layer within the outer cover.

Example 12

In this Example, the noise produced by a PREVAIL youth pant (size 40-70 lbs), manufactured in 2002 and available from First Quality Enterprises, a company having offices in Great Neck, N.Y., was quantified. This product included a full-length, thermoplastic, polymeric film layer within the outer cover.

Example 13

In this Example, the noise produced by a MOTS D'ENFANTS training pant (size 15-25 kg), purchased in France and manufactured in 2001 by SCA, a corporation having offices in France, was quantified. This product included a full-length, thermoplastic, polymeric film layer within the outer cover.

Example 14

In this Example, the noise produced by a MAMY POKO training pant (size 12+ kg), purchased in Thailand and manufactured in 2003 by the Unicharm corporation, a corporation having offices in Seattle, Wash., was quantified. This product included a full-length, thermoplastic, polymeric film layer within the outer cover.

Example 15

In this Example, the noise produced by a GOO.N training pant (size 7-12 kg), purchased in Japan and manufactured in 2003 by the Daio Paper Company, a company having offices in Japan, was quantified. This product included a full-length, thermoplastic, polymeric film layer within the outer cover.

Example 16

In this Example, the noise produced by a prototype reduced-noise youth pant was quantified. The prototype was identical to the product tested in Example 5, with the exception that the full-length thermoplastic, polymeric backsheet layer and the outermost nonwoven layer were laminated together with hot-melt construction adhesive available from the National Starch and Chemical Corp., applied using a slot-coat application as discussed earlier. The slot-coat adhesive was applied to approximately 96 percent of the surface area of the thermoplastic, polymeric backsheet layer at an add-on rate of approximately 20 grams per square meter. The entire product was machine-made.

Example 17

In this Example, the noise produced by a prototype reduced-noise youth pant was quantified. All of the materials used to make this prototype were identical to those used to produce the product tested in Example 16, but the pant was handmade, rather than machine-made. The various components of the youth pant were affixed to each other using a construction adhesive available (stock no. 34-5610) available from National Starch and Chemical Corp., at an add-on rate of approximately two to four grams per square meter.

Example 18

In this example, the noise created by an experimental laminate was measured. The laminate was constructed of materials commonly found in training and youth pants.

By way of background, PULL-UPS® GOODNITES® youth pants include a laminate outer cover having two layers, one of which is a thermoplastic, polymeric film and the other of which is a spunbond material. It is believed that as the thermoplastic, polymeric layer is manipulated, in large part by the tensioning forces exerted by the elastics within the product, noise is produced by the buckling of the polymeric layer. In an attempt to isolate the noise impact of the outer cover and other materials, experimental laminates were constructed to approximate the outer cover, liner, and leg elastic portions of a Large size (65-85 lb) PULL-UPS® GOODNITES® youth pant. Specifically, a web of polypropylene spunbond nonwoven material having a basis weight of 1.0 ounces per square yard was laminated to a polyethylene film having a basis weight of approximately 14 ounces per square yard and thickness of 0.75 mils. Each material was 23 inches (584 mm) long and 6.5 inches (165 mm) wide. The nonwoven material is available from Kimberly-Clark Corporation, and the polyethylene film is available from Pliant Corp., a business having offices in Chippewa Falls, Wis., U.S.A. The lamination was accomplished using construction adhesive (stock no. 34-5610) available from National Starch and Chemical Corp., applied to the entirety of the film layer using a swirl hot-melt adhesive applicator at an add-on rate at approximately two grams per square meter. A strip of two-sided tape, available from the Minnesota Mining and Manufacturing Corp., a company having offices in Minneapolis, Minn., U.S.A., 6.35-millimeters wide and 209 millimeters long, was used to affix two 209 millimeters long (fully elongated state) (89 millimeters long (relaxed state)) stranded elastic laminate to the polymeric-film side of the nonwoven-film laminate. The stranded elastic laminate placed on each side comprised two strands of 940 decitex Lycra elastic, available from DuPont Corp. of Wilmington, Del., U.S.A., spaced four mm from each other, sandwiched between two layers of 0.55 ounces per square yard polypropylene spunbond material, using H2800 rubber-based hotmelt lamination adhesive, available from the Bostik Findley Corp. The strands were laminated at 300% elongation. The sandwiching spunbond layers were each 209 millimeters long. The outer edge of each elastic-laminate strip was affixed to the polyethylene film surface 30 millimeters in from and parallel to opposite longitudinal edges of the polyethylene film, at 135 percent elongation (89 mm stretched to 209 mm). A layer of bodyside liner materials measuring 584-millimeter by 165-millimeter and formed of 0.55 ounces per square yard polypropylene spunbond nonwoven was affixed atop the elastic strands, accomplished using construction adhesive (stock no. 34-5610) available from National Starch and Chemical Corp., applied to the entirety of the liner layer using a swirl hot-melt adhesive applicator at an add-on rate at approximately two grams per square meter.

Example 19

In this example, the noise created by an experimental laminate identical to that tested in Example 18 was tested, except that the construction adhesive was applied to the entirety of the polyethylene layer via a continuous slot-coat applicator, at a basis weight of approximately 20 grams per square meter.

TABLE

Noise Produced By Examples (in dB)

| Ex. | | 2 kHz | | 4 kHz | |
|---|---|---|---|---|---|
| | | Avg | StdDev | Avg | StdDev |
| 1 | Inside the test chamber, motor off | 17.4 | 0.07 | 16.4 | 0.09 |

TABLE-continued

Noise Produced By Examples (in dB)

|     |     | 2 kHz | | 4 kHz | |
| --- | --- | --- | --- | --- | --- |
| Ex. |     | Avg | StdDev | Avg | StdDev |
| 2 | Inside the test chamber, motor on | 25.5 | 0.16 | 21.6 | 0.13 |
| 3 | LUVS SLEEPDRYS youth pant | 35.2 | 0.96 | 32.3 | 0.46 |
| 4 | PULL-UPS ® GOODNITES ® youth pant, polymeric film within flaps | 38.0 | 0.27 | 38.2 | 0.25 |
| 5 | PULL-UPS ® GOODNITES ® youth pant, no polymeric film within flaps | 32.4 | 0.64 | 31.3 | 0.30 |
| 6 | PAMPERS EASY UPS training pant | 30.7 | 0.49 | 28.9 | 0.49 |
| 7 | HUGGIES ® PULL-UPS ® training pant | 34.5 | 0.46 | 33.8 | 0.56 |
| 8 | TORE PAN MAN training pant | 34.3 | 0.35 | 34.8 | 0.30 |
| 9 | WALGREEN'S training pant | 33.1 | 0.65 | 37.4 | 1.51 |
| 10 | CVS youth pant | 34.4 | 0.92 | 36.2 | 1.26 |
| 11 | WHITE CLOUD training pant | 34.8 | 0.95 | 36.4 | 0.81 |
| 12 | PREVAIL youth pant | 35.6 | 2.33 | 38.0 | 1.09 |
| 13 | MOTS D'ENFANTS training pant | 42.1 | 0.68 | 43.3 | 0.53 |
| 14 | MAMY POKO training pant | 37.7 | 0.76 | 37.8 | 1.21 |
| 15 | GOO.N training pant | 33.4 | 1.68 | 32.3 | 0.89 |
| 16 | Prototype youth pant, with slot-coat noise-reducing coating (machine made) | 29.9 | 0.50 | 27.7 | 0.32 |
| 17 | Prototype youth pant, with slot-coat noise-reducing coating (hand made) | 32.2 | 0.73 | 30.4 | 0.86 |
| 18 | Handmade experimental laminate (youth pant-style outer cover/leg elastic/liner laminate) - 5 gsm spray adhesive | 33.4 | 0.58 | 34.7 | 0.44 |
| 19 | Handmade experimental laminate (youth pant-style outer cover/leg elastic laminate) - 20 gsm slot-coat adhesive | 28.5 | 0.53 | 25.4 | 0.71 |

As the Table illustrates, most specimens lacking the appropriate noise-reducing coating produced higher levels of noise at each of the two frequencies tested to which the human ear is highly sensitive (2 and 4 kHz) as compared to the specimens treated with a noise-reducing material. For example, the PULL-UPS® GOODNITES® youth pant of Example 5, which contained a thermoplastic, polymeric outer cover layer but lacked a noise-reducing coating material, produced noise levels of 32.4 dB at 2 kHz, and 31.3 dB at 4 kHz. In contrast, the prototype but similar youth pant of Example 16, which contained the same thermoplastic, polymeric outer cover layer but included the noise-reducing coating material of the present invention, produced noise levels of 29.9 dB at 2 kHz, and 27.7 dB at 4 kHz. As decibels are a logarithmic unit of measurement, this is a significant reduction in noise energy. Similarly, the sprayed laminate of Example 18 produced noise levels of 33.4 dB at 2 kHz, and 34.7 dB at 4 kHz, compared with the slot-coated laminate of Example 19, which produced noise levels of 28.5 dB at 2 kHz, and 25.4 dB at 4 kHz. Again, since decibels are a logarithmic unit of measurement, this is a significant reduction in noise energy. The "Noise Level" or "Sound Level" of an article as those phrases are used herein refers to the noise or sound measured when the article is analyzed using the testing apparatus and procedure described above.

The invention claimed is:

1. A disposable absorbent article comprising:
    a body-side liner;
    a garment-side outer cover, said outer cover comprising a liquid-impermeable substrate layer comprised of a thermoplastic, polymeric material and which defines a first surface having a surface area; a noise-reducing layer which substantially completely coats a target region of said first surface; and
    an absorbent assembly disposed between said body-side liner and said garment-side outer cover,
wherein the article has a Noise Level of less than 30.0 dB at 2 kHz and less than 28.0 dB at 4 kHz.

2. The disposable absorbent article of claim 1, wherein the target region has an area which is at least about 50% of said surface area;
    said noise-reducing layer having a basis weight of at least about three grams per square meter.

3. The disposable absorbent article of claim 2 wherein said noise-reducing layer consists essentially of at least one of polyisoprene, polybutadiene, polyisobutylene, polyurethanes, silicone rubber, atactic polypropylene, and a synthetic block co-polymer.

4. The disposable absorbent article of claim 1 wherein said substrate layer comprises a non-elastomeric thermoplastic, polymeric material.

5. The disposable absorbent article of claim 4 further comprising a nonwoven layer adhered to said substrate layer.

* * * * *